United States Patent
Armstrong et al.

(10) Patent No.: US 6,255,294 B1
(45) Date of Patent: Jul. 3, 2001

(54) CYANOCOBALAMIN (VITAMIN B12) TREATMENT IN ALLERGIC DISEASE

(75) Inventors: Hepburn T. Armstrong, Vista; John A. Wise, San Marcos; Ernest T. Armstrong, San Diego, all of CA (US)

(73) Assignee: Allergy Limited, Costa Mesa, CA (US)

( * ) Notice: Subject to any disclaimer, the term of this patent is extended or adjusted under 35 U.S.C. 154(b) by 0 days.

(21) Appl. No.: 09/473,332

(22) Filed: Dec. 28, 1999

Related U.S. Application Data

(60) Provisional application No. 60/113,896, filed on Dec. 28, 1998.

(51) Int. Cl.$^7$ .................................................. A61K 31/70
(52) U.S. Cl. ............................................. 514/52; 536/26.4
(58) Field of Search ................................ 514/52; 536/26.4

(56) References Cited

U.S. PATENT DOCUMENTS

| | | | |
|---|---|---|---|
| 4,724,231 | * | 2/1988 | Wenig ........................................ 514/52 |
| 4,927,850 | * | 5/1990 | Bayless et al. ....................... 514/458 |
| 5,135,918 | * | 8/1992 | Peraita .................................... 514/52 |
| 5,508,282 | * | 4/1996 | Tulin-Silver et al. ............... 514/264 |
| 6,066,333 | * | 5/2000 | Willis et al. .......................... 424/464 |

FOREIGN PATENT DOCUMENTS

| | | | |
|---|---|---|---|
| 0754450 | * | 1/1997 | (EP) . |
| 5139959 | * | 6/1993 | (JP) . |
| 9916417 | * | 4/1999 | (WO) . |

OTHER PUBLICATIONS

Berkow et al. (eds.), *The Merck Manual of Diagnosis and Therapy, 16th Edition*, Merck & Co., Rahway, NJ, May, 1992, only pp. 326–327 and 2345–2348 supplied.*

*Taber's Cyclopedic Medical Dictionary, 17th Edition*(iIllustrated), F. A. Davis Company, Philadelphia, PA, 1989, only pp. 70–71, 1720–1721 and 1804 supplied.*

Berkow et al. (eds), *The Merck Manual of Diagnosis and Therapy, 16th Edition*, Merck & Co., Rahway, NJ, May, 1992, only pp. 1156–1158 supplied.*

Benet et al., "Pharmacokinetics: The Dynamics of Drug Adsorption, Distribution, and Elimination", Chapter 1 in *Goodman and Gilman's The Pharmacological Basis of Therapeutics, 8th Edition*, Gilman et al.(eds), Pergamon Press, New York, NY, 1990, only pp. 3–10 supplied.*

* cited by examiner

*Primary Examiner*—Gary Geist
*Assistant Examiner*—L. E. Crane
(74) *Attorney, Agent, or Firm*—Greer, Burns, & Crain, Ltd.

(57) ABSTRACT

Vitamin $B_{12}$ is administered to allergy patients via mucosal membranes in a series of lozenges and other patient friendly transmucosal modes of delivery given repeatedly over a period of time to reduce the symptoms and IgE antibodies associated with allergic diseases such as allergic rhinitis (hay fever), and allergic asthma.

11 Claims, No Drawings

CYANOCOBALAMIN (VITAMIN B12) TREATMENT IN ALLERGIC DISEASE

CROSS REFERENCE

This application is a continuation-in-part of U.S. Provisional Application No. 60/113,896, filed Dec. 28, 1998.

TECHNICAL FIELD

The invention relates to the use of nutritional supplements to treat disease. It relates particularly to treatment of IgE-type allergies, such as allergic rhinitis (hayfever) and allergic asthma, by the repeated administration over a period of time of vitamin $B_{12}$, preferably cyanocobalamin, to reduce the symptoms associated with such allergic diseases.

BACKGROUND ART

The symptoms of allergic diseases, such as allergic rhinitis (hay fever) and allergic asthma, can be caused by a variety of atopic allergens, such as grasses, trees, weeds, animal dander, insects, molds, drugs and chemicals. These allergic diseases are mediated by an antibody known as immunoglobulin E, or simply IgE. Anti-IgE medicines that reduce IgE levels are attractive treatments for allergy patients.

IgE bonds to mast cells and basophils. Upon combination of a specific allergen with IgE bound to mast cells or basophils, the IgE may be crosslinked on the cell surface, resulting in the physiological effects of IgE-antigen interaction. This may result in the release of histamine, serotonin, heparin, a chemotactic factor for eosinoplylic leukocytes and/or the leukotrienes, C4, D4 and E4, which cause prolonged constriction of bronchial smooth muscle cells. These released substances are the mediators which result in allergic symptoms.

Vitamin $B_{12}$ is essential to cell growth, cell reproduction, hematopoiesis, DNA synthesis and nucleoprotein synthesis. Deficiencies in Vitamin $B_{12}$ or folic acid can lead to the inhibition of normal cell division and abnormal maturation and functioning of cells produced. These changes are most apparent in cells that undergo rapid mitosis (cell division), but all dividing cells are affected to some degree. In patients with Vitamin $B_{12}$ or folic acid deficiency, pancytopenia (diminished production of red blood cells, white blood cells and platelets) may occur. The U.S. Food and Drug Administration (FDA) recognized the description of this problem on the molecular level in its approval of $B_{12}$ for anemia.

The mechanism of action for Vitamin $B_{12}$ in IgE-mediated allergic diseases, such as allergic rhinitis and asthma, may involve the maturation of certain immune system cells including polynucleated cells, natural killer (NK) cells, and CD8+ cells. The CD8+ cell is an immune system T lymphocyte believed to "put the brakes on" the immune system, making the allergy patient less sensitive to allergens such as pollen, cats, and mold. Typically, allergic individuals have numbers of the CD8+ suppressor cells that are low relative to CD4 aggressor cells. These immune system cells may require a sustained and elevated serum Vitamin $B_{12}$ concentration to develop from an immature state to a mature state in which they can exert their down-regulatory function on the immune system. Polynucleated cells are known to have memories that last many years, a concept consistent with controlled studies demonstrating reductions in symptoms and in specific IgE levels persisting many months after parenteral Vitamin $B_{12}$ treatment.

When Vitamin $B_{12}$ is delivered parenterally, it passes into the circulation for distribution throughout the body before arriving at the liver. It is during this first pass in its native form that it is believed to exert its therapeutic effect.

Studies indicate that ingested oral cyanocobalamin is ineffective in the treatment of allergic disease, perhaps because once ingested, it goes directly to the liver where it metabolized. The ineffectiveness may also be caused by poor absorption. Gastrointestinal absorption of Vitamin $B_{12}$ depends on the presence of sufficient intrinsic factor and calcium ions. Its absorption may be hindered by the presence of large amounts of Vitamin C. Tens of millions of people have diets rich in Vitamin $B_{12}$ (from animal products or supplements) and continue to suffer from allergic rhinitis and/or asthma.

Cyanocobalamin is the most widely sold analogue of Vitamin $B_{12}$, with other similar molecules also available. Cyanocobalamin is found in injectable and oral modes of delivery, and has the advantage over other types of $B_{12}$ of having a stable shelf life at standard temperature and pressure (STP).

The analogues of Vitamin $B_{12}$ are the only molecules used by the human body that contain cobalt. The empirical formula of cyanocobalamin is: $C_{63}H_{88}CoN_{14}O_{14}P$.

U.S. Pat. No. 5,135,918, which is owned by the applicant, Allergy Limited LLC, discloses a highly effective method of achieving long term relief from the symptoms of atopic allergy by repeated subcutaneous and/or intramuscular injections of $B_{12}$ over a short period of time. In practice, the treatment has comprised thirty injections of $B_{12}$, preferably cyanocobalamin, administered twice daily over a period of fifteen days. This series of 30-injections has been successful from a point of view of efficacy in treating allergic disease, but has resulted in subjects reporting bruising and/or soreness at the local injection site. The difficulties involved in having the patient go into a medical clinic 30 times over a fifteen-day period for injections are numerous. However, providing patients with syringes for self-injection also poses problems. Once a syringe has been used it is contaminated and must be disposed of in a biohazard container or there is risk of transmitting diseases such as hepatitis or the HIV virus. Concerns have been raised about the possibility of cross-contamination of vials by lay allergy patients with minimal medical knowledge who self-inject. Both the manufacture and disposal of syringes are environmentally hazardous.

DISCLOSURE OF THE INVENTION

It is the primary object of the present invention to provide patient-friendly modes of delivery to patients of effective allergy-opposing amounts of Vitamin $B_{12}$ without the inconvenience and discomfort of subcutaneous and intramuscular injections.

It is in particular an object of the invention to provide for enhanced delivery of effective amounts of $B_{12}$ via the mucosal membranes of the patient, i.e., the mouth, nose, anus and vagina.

A further object of the invention is to provide a method for treating allergies by repetitive administration over a period of time via transmucosal delivery of amounts of Vitamin $B_{12}$ effective to maintain an elevated and sustained level of $B_{12}$ in the system sufficient for the reproduction and maturation of polynucleated cells and CD8+ suppressor cells so they can exert their down-regulatory function on the immune system.

In accordance with the invention, vitamin $B_{12}$ is instilled in a carrier matrix, such as controlled release lozenges, chewing gum, nasal sprays, douches and suppositories, for patient-friendly, self-administration of effective allergy-opposing amounts of vitamin $B_{12}$. The invention thereby minimizes inconvenience and discomfort for the patient and alleviates the burden and time demands imposed on medical staff.

These and other objects and advantages of the invention will become apparent to those of reasonable skill in the art from the following detailed description.

BEST MODE FOR CARRING OUT THE INVENTION

The following is a detailed description of certain embodiments of the invention which are presently deemed by the inventors to be the best mode of carrying out the invention. Unless otherwise stated, the following terms used in the specification and claims have the meanings given below:

"Delivery" refers to the passage of a substance across or through a mucosal membrane (i.e.) sublingual, buccal, nasal, pulmonary, vaginal, and anal membranes), where the substance can contact, and be absorbed into, the capillaries. In certain instances, the delivery and/or transport of the substance across other membranes will be effected.

"Buccal delivery" refers to any system or device for the oral administration of a drug to a patient that is held in the mouth and is used to deliver a drug through the buccal mucosa and into the patient's body. "Sublingual delivery" refers to administration under the tongue. These terms include, but are not limited to, lozenges, capsules, tablets, and gum.

"Enhanced delivery" refers both to the facilitation of the delivery of a pharmaceutical agent and an absolute increase in the molar volume of the pharmaceutical agent transported per unit time through a constant surface area utilizing an equimolar pool of transported material as compared to unenhanced delivery.

"Penetration enhancer" refers to a substance which is used to increase the transmembrane flux of a compound. A penetration enhancer is typically applied to the mucous membrane in combination with the compound. Enhancers are believed to function by disrupting the mucous membrane barrier or changing the partitioning behavior of the drug in the mucous membrane.

"Allergy-opposing, pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system.

The present invention provides several embodiments of transmucosal delivery systems containing any of the analogues of Vitamin $B_{12}$ (cobalamin). The analogues include but are not limited to cyanocobalamin, hydroxycobalamin, adenosylcobalamin, deoxyadenosylcobalamin and methylcobalamin as well as their respective metabolites. The preferred Vitamin $B_{12}$ is cyanocobalamin. The invention comprises the use of the Vitamin $B_{12}$-containing delivery systems in the treatment of IgE-related allergic disease.

The delivery systems comprise a $B_{12}$ containing matrix material compatible with the mucosal membrane into which the vitamin $B_{12}$ is to be absorbed, e.g., a lozenge or tablet for buccal ingestion, a spray of salve for nasal ingestion, a suppository for anal absorption, and a suppository, douche or cream for vaginal absorption. The matrix material also preferably includes a time controlled or slow release mechanism or agent and a penetration enhancer for stimulating the respective mucosal membrane to enhance absorption of the $B_{12}$ into the patient's system. Several such matrix materials are described in the literature.

A presently preferred oral matrix material is the lozenge developed by TheraTech of Salt Lake City, Utah, (a subsidiary of Watson Labs) which is described in U.S. Pat. No. 5,346,701. The lozenge is formulated to provide maximum absorption of macromolecules. For convenience of administration and testing of oral delivery of the $B_{12}$, from about 1,000 to about 5,000 micrograms (mcg) of cyanocobalamin may be instilled in each TheraTech lozenge. The dosage can be more or less, as desired. According to a preferred embodiment, the lozenge is round with a diameter of approximately 1.8 cm (a little smaller than a U.S. dime) and is flavored.

A presently preferred method for treating allergic disease with the $B_{12}$ infused TheraTech lozenges comprises administration of from 1,000 to 3,000 (mcg) of $B_{12}$ twice daily over a period of twenty-one days. The duration of treatment may be increased or decreased depending upon each patient's response to the treatment.

To facilitate self-practice of the method, a preferred embodiment of a product comprises a kit containing forty-two of the $B_{12}$ lozenges and forty-two multivitamin supplements, preferably capsules or tablets each containing:

| | | |
|---|---|---|
| $B_1$ | thiamine mononitrate | 25 mg |
| $B_2$ | riboflavin | 25 mg |
| $B_6$ | pyridoxine HCL | 25 mg |
| $B_3$ | niacin | 20 mg |
| | manganese | 6 mg |
| C | ascorbic acid | 500 mg |

Optionally, folic acid (folate) may be included. Folic acid is chemically unrelated to Vitamin $B_{12}$ but the two are integral to the same pathway that produces nucleotides needed for DNA synthesis. Folic acid is readily absorbed from oral supplementation. Manganese is a mineral that aids in converting cyanocobalamin into its active form (the metabolite). The vitamin C may be included with the other oral vitamins or separate.

Optionally, each capsule or tablet may also contain the herb Stinging Nettle (from Urtica dioica). In a preferred formula, each capsule contains about 50 mg from the leaf of the Stinging Nettle plant, and is present as standardized 1–2% plant silica. In another formulation, each capsule contains about 10–100 mg of extract of the root of the plant. The manganese and the other oral supplements can each be provided as part of the treatment for allergic disease in either the oral capsule or tablet, or made part of the lozenge.

The lozenge is formulated to dissolve completely in the mouth for $B_{12}$ absorption by the buccal membrane.

According to another preferred embodiment of the $B_{12}$ delivery system of the invention, an effective allergy opposing amount of Vitamin $B_{12}$, e.g., 1,000–5,000 mcg, may be incorporated in controlled release chewing gums of the type used to deliver nicotine, such as the chewing gums sold under the trademarks Nicorrette and Nicotrol. This delivery form provides the affected individual with ease of use and proper absorption.

The invention thus provides a simple and convenient mode of administration of an effective amount of $B_{12}$ to provide allergy sufferers with an elevated and sustained level of Vitamin $B_{12}$ to alleviate their allergy symptoms.

Because of the obvious improvements in patient compliance and acceptability of a series of lozenges over a series of injections, the applicant sponsored a study to compare the absorption of the above-described $B_{12}$ infused TheraTech lozenges to the absorption of a 15 mcg injectable administered as described in U.S. Pat. No. 5,135,918.

Baseline Subjects EA (38, M, 175 lbs), HW (42, M, 330 lbs), AG (36, F, 130 lbs) and JS (50, M. 165 lbs) had blood drawn at Quest Laboratories in San Diego, Calif. Samples sat for 30 min, and had sera removed. Sera were chilled in a refrigerator.

Baseline Subject EA then received a 15 mcg cyanocobalamin injection via intramuscular injection in the left deltoid.

Subject HW received one TheraTech lozenge with 1000 mcg cyanocobalamin. He let it dissove completely in his mouth (under and above the tongue) for 30 minutes.

Subject AG received two TheraTech lozenges with 1000 mcg cyanocobalamin each. She let them dissolve completely in her mouth. She scraped the lozenges with her teeth to expedite dissolving.

Subject JS received three TheraTech lozenges with 1000 mcg cyanocobalamin each. He let them dissolve completely in his mouth. He sucked on the lozenge for a few minutes, chewed the lozenge and then let the little pieces dissolve in his mouth.

Approximately one hour after receiving treatment (post-dose), subjects EA, HW, AG and JS had blood drawn.

Approximately four and a half hours after receiving treatment, subjects AG and JS had blood drawn.

Approximately six hours after receiving treatment, subjects EA and HW had blood drawn.

Samples were assayed in different runs using the competitive automated Chemiluminescence System VB12 from Chiron Diagnostics for the quantitative determination of $B_{12}$ in serum. Results: (Serum $B_{12}$ values are in pg/mL, with a reference range of 200–1100.)

| EA | HW | AG | JS |
|---|---|---|---|
| 15 mcg Injected<br>% Increase | 1000 mcg Lozenge<br>% Increase | 2000 mcg Lozenge<br>% Increase | 3000 mcg Lozenge<br>% Increase |
| BASELINE 709 | 333 | 399 | 371 |
| 1 HR 1021 44% | 386 16% | 458 15% | 394 6% |
| 4.4 hrs. 576 26% | 531 35% | | |
| 6hrs. 915 33% | 387 16% | | |

It appears that a lozenge containing 3000 mcg cyanocobalamin provides a similar but somewhat more sustained release than a 15 mcg injection, which provides a spiked release less than an hour after injection. If the mechanism involves CD8+ suppressor cells and/or polynucleated cells in need of an elevated $B_{12}$ level sustained over the course of 15 days or more to mature, then the lozenge is preferable.

Cyanocobalamin has been reviewed for safety and approved by the FDA to be injected in high doses (1000 to 5000 mcg). A twice-daily 3000 mcg lozenge with the TheraTech absorption profile provides less of an increase in serum cyanocobalamin than a 50 or 100 mcg injection.

In view of the above results, a multi-site clinical trial was undertaken (1) to determine whether cyanocobalamin delivered orally via a TheraTech lozenge, and taken concomitantly with oral vitamins can decrease symptoms in patients with seasonal allergic rhinitis, and (2) to determine and monitor the effects of the treatment in regard to certain selected safety issues.

This was a double blind, placebo controlled, randomized, parallel group, premarketing study comparing active Vitamin $B_{12}$ therapy and placebo in patient volunteers who had moderate to moderately sever seasonal allergic rhinitis (hay fever). The results showed an active-group reduction in sneezing, runny nose and antihistamine use which persisted for weeks after the end of the treatment.

The subjects self-administered cyanocobalamin lozenges or placebo at approximately twelve-hour intervals in the morning and the evening daily for twenty-one consecutive days. All subjects received oral multivitamin supplements taken each morning and evening. Patients were not permitted to have had a systemic corticosteriod treatment for one month prior to beginning the treatment or to use other allergy medications during the treatment, but were permitted to continue immunotherapy (allergy shots) if they were on maintenance doses. For compassion reasons, patients were permitted to take up to 16 mgs of an H1 antihistamine per day, provided to them as a rescue medication. This was 4 mg chlorpheniramine (CPM).

The study took place at four medical clinics in San Diego, Calif. durnig the spring and summer of 1998. The San Diego area pollen counts in 1998 were high relative to most years, possibly because of strong El Nino weather patterns.

Each patient recorded the severity of runny nose, sneezing, nasal congestion, itchy eyes and nasal itch in the AM and PM daily during an initial one-week baseline period, during the three week treatment period, and for an additional five weeks. Severity was recorded on a scale of 0 to 3, with 0 meaning symptom free and 3 meaning severe discomfort.

The study was completed with 24 valid male and female patient volunteers, ages 12 to 80; 15 on the active lozenge and 9 on the placebo.

The medications administered were dietary supplements, in a kit comprising 42 TheraTech lozenges each containing 3000 mcg cyanocobalamin or like appearing placebos. Natural Alternatives International, Inc., San Marcos, Calif. manufactured the lozenges and capsules. Each active and placebo subject also received 42 capsules, each containing:

| $B_1$ | thiamine mononitrate | 25 mg |
|---|---|---|
| $B_2$ | riboflavin | 25 mg |
| $B_3$ | niacin | 50 mg |
| $B_6$ | pyridoxine HCL | 25 mg |
| | manganese | 6 mg |

Each active and placebo subject also received 42 capsules, each containing:

| C | ascorbic acid | 500 mg |
|---|---|---|

Each active and placebo subject also received a bottle of chorpheniramine (CPM) 4 mg antihistamine as rescue medication.

The results of the study yielded reductions in total weekly symptom/rescue medication for the active group compared to the placebo for weeks 2, 6, 8 and 9. In results which tend to replicate those of the injectable cyanocobalamin, symptoms in the active and placebo groups dropped during the treatment, followed by a resumption of symptoms during the post-treatment period in the placebo group but not in the active group. This persistence of effect in the active group was greater for sneezing, runny nose and antihistamine use than for nasal congestion, nasal itch and itchy eye.

The twenty-four subjects who completed the diary as valid subjects (active=15, placebo=9) reported the following scores. Total symptons scores are the weekly means for the active and placebo groups for each patient-reported symptom on a scale of 0 to 3. Rescue medication is the weekly mean of CPM use, with each 4 mg tablet consumed given a value of 1.

Frequency of Increase or Decrease in Total Sympton/Rescue Medication Use

| | Week 1 (Baseline) Compared to Week 2 | | Week 1 Compared to Week 3 | |
|---|---|---|---|---|
| | Increase | Decrease | Increase | Decrease |
| Active | | | | |
| No. Subjects: | 3 | 12 | 3 | 12 |
| Percentage: | 20% | 80% | 20% | 80% |
| Placebo | | | | |
| No. Subjects: | 5 | 4 | 3 | 6 |
| Percentage: | 56% | 44% | 33% | 67% |
| Chi-Square Probability | 0.074 | | 0.465 | |

| | Week 1 Compared to Week 4 | | Week 1 Compared to Week 5 | |
|---|---|---|---|---|
| | Increase | Decrease | Increase | Decrease |
| Active | | | | |
| No. Subjects: | 2 | 13 | 2 | 13 |
| Percentage: | 13% | 87% | 13% | 87% |
| Placebo | | | | |
| No. Subjects: | 3 | 6 | 2 | 7 |
| Percentage: | 33% | 67% | 22% | 78% |
| Chi-Square Probability | 0.243 | | 0.572 | |

| | Week 1 Compared to Week 6 | | Week 1 Compared to Week 7 | |
|---|---|---|---|---|
| | Increase | Decrease | Increase | Decrease |
| Active | | | | |
| No Subjects: | 1 | 14 | 4 | 11 |
| Percentage: | 7% | 73% | 27% | 73% |
| Placebo | | | | |
| No. Subjects: | 4 | 5 | 4 | 5 |
| Percentage: | 44% | 56% | 44% | 56% |
| Chi Square Probability | 0.027 | | 0.371 | |

| | Week 1 Compared to Week 8 | | Week 1 Compared to Week 9 | |
|---|---|---|---|---|
| | Increase | Decrease | Increase | Decrease |
| Active | | | | |
| No. Subjects: | 1 | 14 | 3 | 12 |
| Percentage: | 7% | 93% | 20% | 80% |
| Placebo | | | | |
| No. Subjects | 4 | 5 | 5 | 4 |
| Percentage: | 44% | 56% | 56% | 44% |
| Chi-Square Probability | 0.027 | | 0.074 | |

There were no reports of adverse events with the exception of an equal number of active and placebo subjects reporting a red rash minutes after taking the treatment. This flushing went away in all cases in approximately an hour. The investigative physicians concurred that this could be attributed to the large amount of niacin (50 mg) in the capsule and the quick release nature of the capsule.

The patient's total weekly symptom/antihistamine use score was calculated by adding all symptom scores and 4 mg antihistamine tablets for any given week. The total weekly symptom/rescue medication score is the mean for all subjects in the group, active or placebo.

The results yielded reductions ($0.1 > p > 0.01$) in total weekly symptom/antihistamine use scores for the active group compared to the placebo group for weeks 2, 6, 8 and 9. The greatest differences appeared in the last two weeks of the study. These reductions in the active group were greatest for sneezing, runny nose and antihistamine use.

In general, approximately one-third of subjects in allergic rhinitis studies report a reduction in symptoms when given a placebo. It can be speculated that the largest differences in symptom/antihistamine use scores reported in the current study were in the last two weeks because the placebo group was reporting a placebo effect during and shortly after the treatment.

The antihistamine used, CPM, is known to reduce the symptoms associated with allergic rhinitis. Adding antihistamine use to the symptom score simplifies the reporting of results but introduces an element with uncertain impact on the results. Knowing what weight to give the antihistamine is problematic and a search of the literature yielded no accepted way to treat the data. Nevertheless, it is important to observe that both antihistamine use and symptoms were reduced in the active group.

The invention thus provides a variety of embodiments of transmucosal $B_{12}$ delivery systems including slow to release wafers, lozenges, tablets, gum and microspheres, sublingual drops and dots, nasal drops and sprays, suppositories, douches, etc., capable of delivering $B_{12}$ to mucosal membranes to be absorbed in the system for therapeutically effective distribution of $B_{12}$ throughout the body before arriving at the liver.

Consequently, elevated and sustained levels of $B_{12}$ can be maintained in the patient's system to alleviate the symptoms of allergic rhinitis and asthma.

The objects and advantages of the invention have therefore been shown to be attained in a convenient, practical, effective and facile manner.

While certain presently preferred embodiments of the invention have been described herein, it is to be appreciated that various changes, modifications, dosage adjustments and additions may be made thereto without departing from the scope of the invention as defined by the appended claims.

What is claimed is:

1. A method for treating atopic allergy in a human host in need thereof comprising delivering to a mucosal membrane of the human for absorption by the membrane and distribution throughout the system of an effective allergy-opposing amount of vitamin B12.

2. A method as set forth in claim 1, comprising delivery by means of a vehicle including a time controlled release agent.

3. A method as set forth in claim 1, comprising delivery by means of a vehicle including a penetration enhancer.

4. A method as set forth in claim 1, comprising delivery to the buccal mucosa of the human by means of one or more lozenges, tablets, wafers, gums, sublingual drops and dots that are dissolved in the mouth.

5. A method as set forth in claim 1, comprising delivery to the nasal mucosa of the human by means of one or more nasal drops, sprays and salves.

6. A method as set forth in claim 1, comprising delivery to the anal mucosa of the human by means of one or more suppositories.

7. A method as set forth in claim 1, comprising delivery to the vaginal mucosa of the human by means of one or more suppositories, douches and creams.

8. A method as set forth in claim 1, comprising repeated delivery to the mucosal membrane over a period of up to twenty-one days of allergy-opposing amounts of vitamin B12.

9. A method as set forth in claim 8, comprising twice-daily delivery over said period.

10. A method as set forth in claim 8, comprising twice-daily delivery over a period of up to twenty-one days as determined by the human's response to treatment.

11. A method as set forth in claim 10, wherein each delivery of vitamin $B_{12}$ comprises from about 1000 to about 5000 micrograms of cyanocobalamin, methylcobalamin or hydroxycobalamin.

\* \* \* \* \*